(12) United States Patent
Otsubo

(10) Patent No.: US 6,293,936 B1
(45) Date of Patent: *Sep. 25, 2001

(54) DISPOSABLE PULL-ON DIAPER

(75) Inventor: Toshifumi Otsubo, Kagawa-ken (JP)

(73) Assignee: Uni-Charm Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/239,563

(22) Filed: Jan. 29, 1999

(30) Foreign Application Priority Data

Jan. 30, 1998 (JP) .................................................. 10-18682

(51) Int. Cl.<sup>7</sup> ..................................................... A61F 13/15
(52) U.S. Cl. ............................................ 604/396; 604/393
(58) Field of Search ................................ 604/378, 385.1, 604/385.2, 393–4, 6; 2/400, 403, 406, 228, 238

(56) References Cited

U.S. PATENT DOCUMENTS

| | | | |
|---|---|---|---|
| 3,807,402 | * | 4/1974 | Miller et al. ........................ 604/378 |
| 4,100,922 | * | 7/1978 | Hernandez ....................... 604/385.1 |
| 4,108,179 | * | 8/1978 | Schaar ............................... 604/385.1 |
| 4,883,481 | * | 11/1989 | Blanchard . |
| 5,052,058 | * | 10/1991 | Mueller ................................. 2/228 |

FOREIGN PATENT DOCUMENTS

| | | |
|---|---|---|
| 37 09 669 C1 | 6/1988 | (DE) . |
| 406200 | 1/1910 | (FR) . |
| 2 269 998 | 3/1994 | (GB) . |
| WO 96/03950 | 2/1996 | (WO) . |
| WO96/03950 | * 2/1996 | (WO) . |

OTHER PUBLICATIONS

Copy of European Search Report, EP 99 30 5170, dated Sep. 29, 2000.

* cited by examiner

Primary Examiner—Anhtuan T. Nguyen
Assistant Examiner—Michael M. Thompson
(74) Attorney, Agent, or Firm—Baker & Daniels

(57) ABSTRACT

A disposable pull-on diaper having of a briefs-type absorbent structure and a trunks-type cover adapted to conceal the absorbent structure. The cover comprises substantially a pair of sheets placed upon each other and at least one of these two sheets is formed with a pair of pleats extending in parallel to and symmetrically of a center line dividing a width of the diaper in two, the one of the pleats presenting a Z-shaped cross-section and the other presenting an inverted Z-shaped cross-section.

4 Claims, 4 Drawing Sheets

DISPOSABLE PULL-ON DIAPER

BACKGROUND OF THE INVENTION

This invention relates to a disposable pull-on diaper for absorbing and containing body exudates.

International Application Disclosure Gazette (Kohyo) WO96/03950 discloses a disposable diaper of double structure type consisting of an inner wear and an outer wear. The inner ware is of briefs-shaped and comprises a liquid-pervious topsheet intended to be in contact with the wearer's skin and a liquid-impervious backsheet intended to be not in contact with the wearer's skin and a liquid-absorbent core disposed between these two sheets. The outer wear is of trunks-shaped made of a nonwoven fabric or a woven fabric and adapted to cover the entire inner wear from outside and thereby to conceal the inner wear. The outer wear has an inner surface of its waist-opening's peripheral edge bonded to the outer surface of the inner wear along its waist-opening's peripheral edge.

The outer wear in the known diaper comprises four fabrics extending vertically of the diaper and transversely opposite side edges of these fabric are bonded to the inner wear along transversely opposite side edges and a middle zone of the diaper so form trunks having a waist-opening and a pair of leg-openings each having a relatively large diameter. The waist-opening has an elastic stretchability in its circumferential direction. The outer wear has relatively many bonding lines and therefore requires much time and labor for manufacturing it. Additionally, many types (and shapes) of fabric must be prepared for manufacturing and may correspondingly lead to increase in the cost.

SUMMARY OF THE INVENTION

In view of the problem as has been described above, it is an object of the invention to provide a disposable pull-on diaper allowing the foregoing problem accompanying the prior art to be effectively eliminated.

According to one embodiment of the invention, there is provided a disposable pull-on diaper comprising an absorbent structure including a liquid-pervious topsheet, a liquid-impervious backsheet and a liquid-absorbent core disposed therebetween so as to form a front body intended to contact the wearer's belly, a rear body intended to contact the wearer's back and a crotch region extending between the front and rear bodies, and a trunks-shaped cover at least partially covering the absorbent structure, wherein: the absorbent structure is folded upon itself along the crotch region with the topsheet inside so as to have opposite side edges extending in a vertical direction of the diaper and longitudinal ends of the front and rear bodies extending between the opposite side edges; the cover comprises a first sheet intended to cover at least partially the front body as well as a front side of the crotch region and a second sheet intended to cover at least partially the rear body as well as a rear side of the crotch region, the first and second sheets respectively having opposite side edges extending in the vertical direction of the diaper and upper and lower edges extending transversely of the diaper, the first and second sheets being bonded to each other along their opposite side edges and transversely middle zones of their lower edges to present trunks-like configuration, and the first and second sheets have respective inner surfaces of their upper edges bonded to front and rear sides of the absorbent structure, respectively; and at least one of the first and second sheets has a pair of pleats extending in the vertical direction and symmetrically with respect to a center line dividing a width of the diaper in two, wherein the pair of pleats have a Z-shaped cross-section and an inverted Z-shaped cross-section, respectively.

According to a another embodiment of the invention, the front and rear bodies are placed flat together and bonded to each other along their side edges so as to present briefs-shaped configuration having a waist-opening and a pair of leg-openings.

According to another embodiment of the invention, the transversely opposite side edges of the absorbent structure placed flat together are interposed between the respective transversely opposite side edges of the cover placed upon each other and these absorbent structure, the first and second sheets are bonded together along their respective associated side edges.

According to still another embodiment of the invention, the longitudinally upper end of the absorbent structure is provided with elastic members extending transversely of the diaper and bonded thereto with an appropriate tension.

DESCRIPTION OF THE PREFERRED EMBODIMENTS

Details of a disposable pull-on diaper according to the invention will be more fully understood from the description given hereunder with reference to the accompanying drawings.

Figure 1:
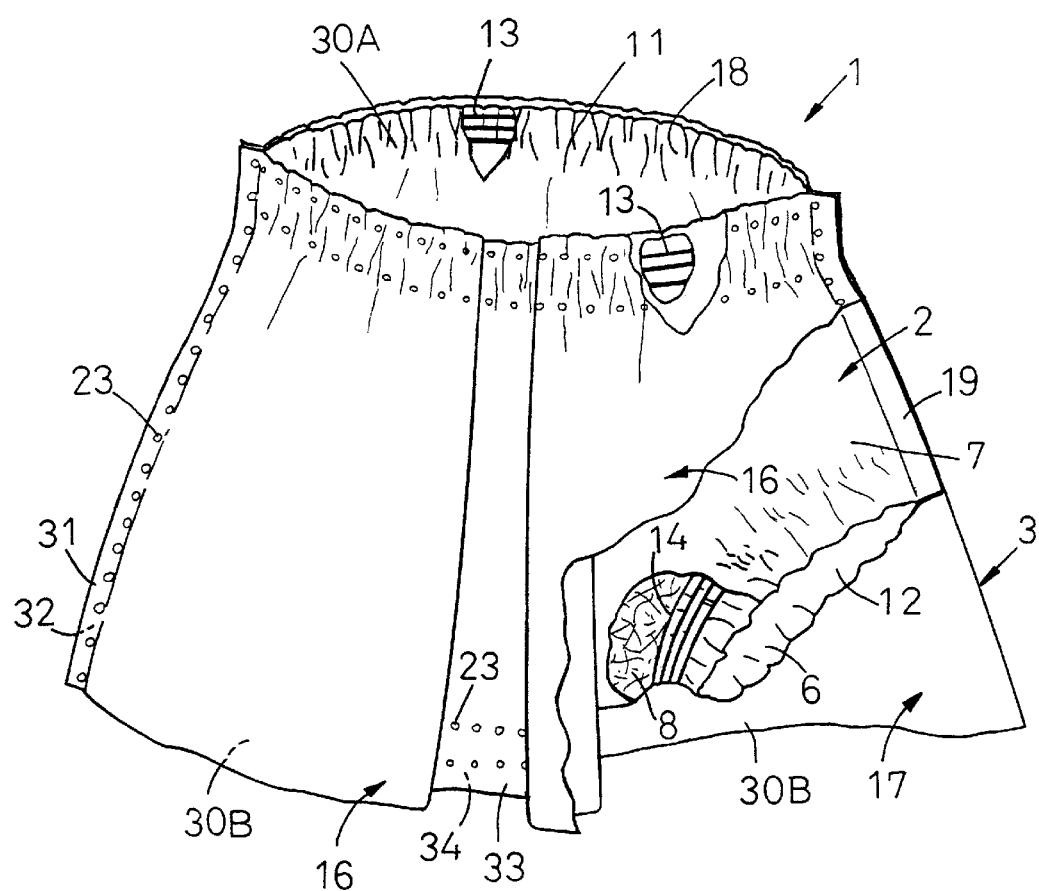
FIG. 1 is a perspective view showing an embodiment of a disposable pull-on diaper according to the invention as partially broken away.

Pull-on diaper 1 shown by FIG. 1 in a perspective view as partially broken away comprises a briefs-shaped absorbent structure 2 extending inside the diaper 1 and a trunks-shaped cover 3 extending outside the diaper 1.

The absorbent structure 2 includes a liquid-pervious innersheet 6, a liquid-impervious outersheet 7 and a liquid-absorbent core 8 disposed between these two sheets 6, 7, so as to form a waist-opening 11 and a pair of leg-openings 12. The respective openings 11, 12 are circumferentially provided with elastic members 13, 14, respectively, which extend between the inner and outersheets 6, 7 and bonded, under appropriate tensions, to an inner surface of at least one of these sheets 6, 7. With the absorbent structure as shown, a plurality of gathers are formed along peripheries of the respective openings 11, 12 as these elastic members 13, 14 contract.

The cover 3 includes a front sheet 16 adapted to cover a front body as well as a front zone of a crotch region being contiguous to the front body of the absorbent structure 2 and a rear sheet 17 adapted to cover a rear body as well as a rear zone of the crotch region being contiguous to the rear body. These sheets 16, 17 are preferably air-pervious sheets each having a size and an opaqueness sufficient to conceal the presence of the absorbent structure 2. The front and rear sheets 16, 17 are placed upon each other with the absorbent structure 2 interposed therebetween and bonded to front and rear surfaces, respectively, of the absorbent structure 2 along a peripheral edge 18 of the waist-opening 11 as well as along transversely opposite side edges 19 of the absorbent structure 2. These front and rear sheets 16, 17 extend downwards beyond a lower end of the absorbent structure 2. The sheets 16, 17 are put flat together and bonded to each other along their transversely opposite side edges 31, 32 of the downward extensions (See FIG. 2) and along their middle portions 33, 34 in a crotch region of the cover 3 (See FIG. 2). A plurality of dots 23 illustrated on these front and rear sheets 16, 17 in FIG. 1 represent locations at which these sheets 16, 17 are bonded to each other and/or to the absorbent structure 2 by means of suitable adhesive agent or heat-sealing technique.

Figure 2:
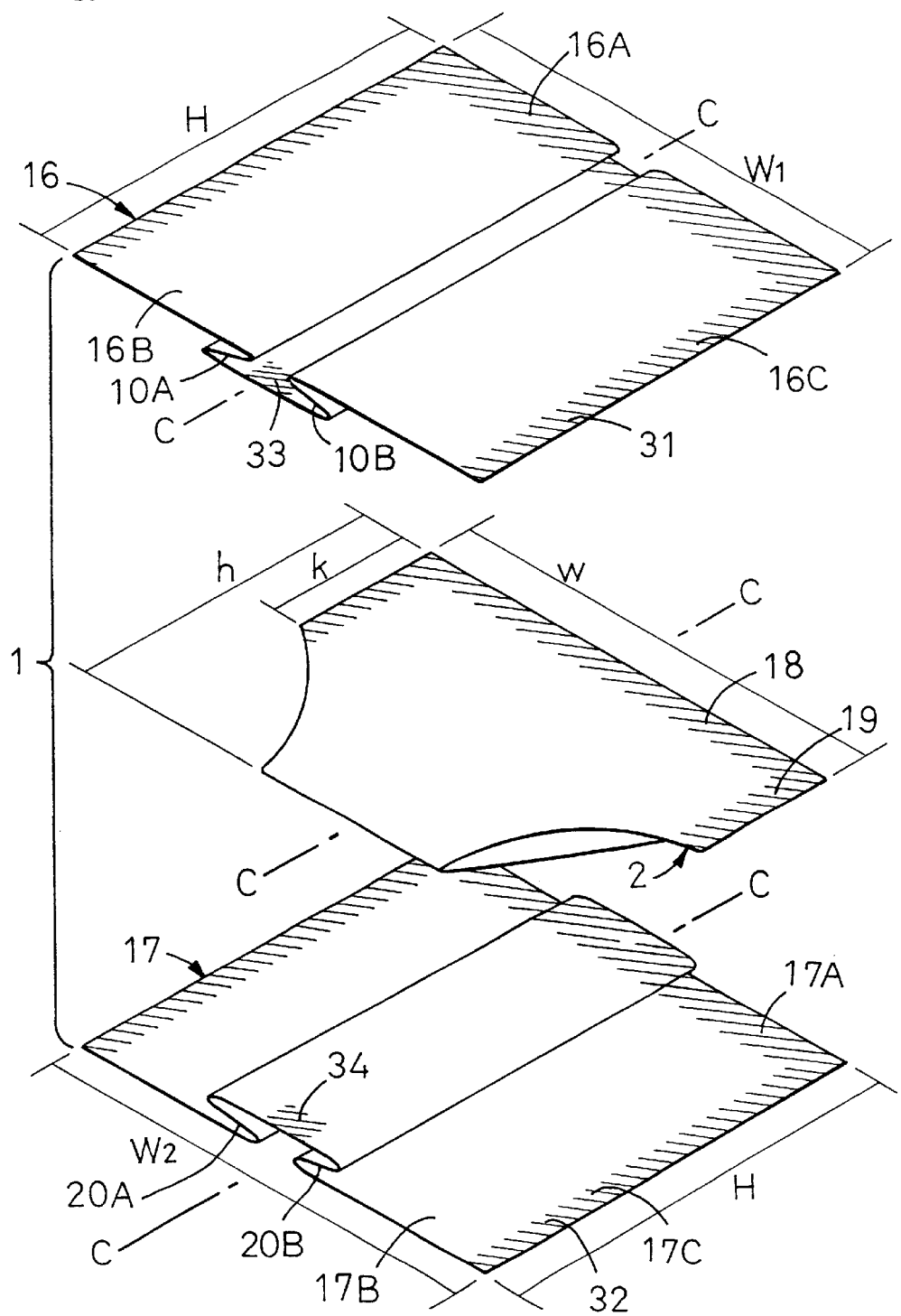
FIG. 2 is an exploded perspective view illustrating the embodiment of the disposable diaper according to the invention.

FIG. 2 is an exploded perspective view illustrating the diaper 1 as its front sheet 16, absorbent structure 2 and rear sheet 17 are separated one from another with the front sheet 16 lying at the uppermost position. The respective elastic members 13, 14 being in their stretched states are not shown. Both the front and rear sheets 16, 17 are folded along a plurality of lines extending in parallel to a center line C—C which extends vertically of the diaper 1 so as to divide a width of the diaper 1 in two. Thus, the front sheet 16 has a pair of pleats 10A, 10B extending in parallel to and symmetrically with respect to the center line C—C and the rear sheet 17 also has a pair of pleats 20A, 20B extending in parallel to and symmetrically with respect to the center line C—C. The pleats 10A, 20B are Z-shaped in their cross-sections and the pleats 10B, 20A are inverted Z-shaped in their cross-sections. The front and rear sheets 16, 17 folded in this manner present same-sized rectangles defined by upper and lower edges 16A, 16B; 17A, 17B extending transversely of the diaper 1 and side edges 16C, 16C; 17C, 17C extending longitudinally of the diaper 1. The upper and lower edges 16A, 16B; 17A, 17B have widths $W_1$, $W_2$, respectively, which may be equal to each other in the illustrated case. The side edges 16C, 16C; 17C, 17C are dimensioned to have one and same height H. Transversely opposite side edges 19 of the absorbent structure 2 has a height k smaller than said height h.

These front and rear sheets 16, 17 have their upper edges 16A, 17A placed upon the front and rear sides, respectively, of the absorbent structure 2 along the peripheral edge 18 of its waist-opening 11 and their side edges 16C, 16C; 17C, 17C placed upon the front and rear sides, respectively, of the absorbent structure 2 along its transversely opposite side edges 19, 19. In this manner, these front and rear sheets 16, 17 are placed upon each other with the absorbent structure 2 disposed therebetween. The front sheet 16 has its edges indicated by hatches on three sides bonded to the belly side (front side) of the absorbent structure 2 along the peripheral edge 18 of the waist-opening 11 and the transversely opposite side edges 19. Similarly, the rear sheet 17 has its edges indicated by hatches on three sides bonded to the back side (rear side) of the absorbent structure 2 along said peripheral edge 18 of the waist-opening 11 and said transversely opposite side edges 19. The front and rear sheets 16, 17 are also directly bonded to each other along the downward extensions 31, 32 of their side edges 16C, 16C; 17C, 17C which extend downwards respectively beyond the side edges 19 of the basic assembly 2. The lower edges 16B, 17B of these sheets 16, 17 are directly placed upon each other and bonded together their middle zones extending in the proximity of the center line C—C.

In regions of the front and rear sheets 16, 17 forming the Z- and inverted Z-cross-section pleats 10A, 10B; 20B, 20A, layers of the front sheet 16 folded onto itself as well as layers of the rear sheet 17 folded onto itself are bonded together along their upper edges 16A, 17A, respectively. On the other hand, these layers of the front sheet 16 folded onto itself as well as layers of the rear sheet 17 onto itself are not bonded together, respectively, along their lower edges 16B, 17B and in the proximity of these lower edges 16B, 17B. More preferably, these folded layers are not bonded together over a large portion of their middle zones inclusive of the lower edges 16B, 17B, respectively. In this state, the front and rear sheets 16, 17 form the cover 3 having a trunks-shaped form (See FIG. 1) serving to cover the absorbent structure 2. The cover 3 has its own waist-opening 30A of the same size as the waist-opening 11 of the basic assembly 2 and its own leg-openings 30B of the size larger than the leg-openings 12 of the absorbent structure 2.

The front and rear sheets 16, 17 of the cover 3 are preferably made of a sheet material being able to conceal the presence of the absorbent structure 2, e.g., a sheet material having a sufficiently low transmissivity or a sufficiently high reflectance or a sufficiently high diffusibility to ensure that the absorbent structure 2 can not be seen through the cover 3. Selection of such sheet material is effective to set a wearer free from any apprehension that the diaper 1 worn by him or her might be perceived by a third person. The leg-openings 30B do not restrict movement of the wearer's legs because the Z- and/or the inverted Z-cross-section pleats 10A, 10B, 20A, 20B are free to flare as the wearer's legs move.

Figure 3:
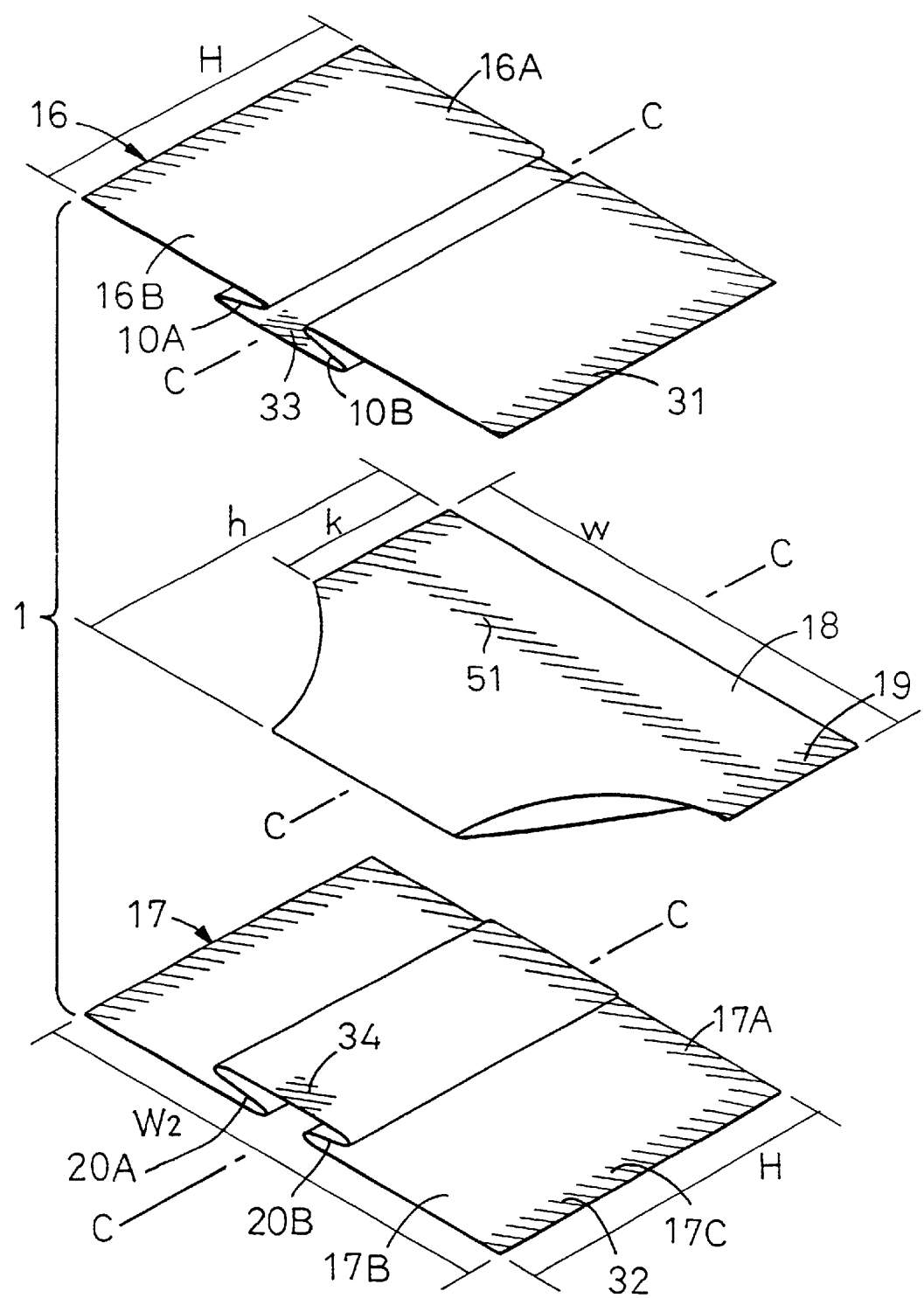
FIG. 3 is a view similar to FIG. 2 illustrating another embodiment of the disposable diaper according to the invention.

FIG. 3 is a view similar to FIG. 2 illustrating an alternative embodiment of the invention. According to this embodiment of the diaper 1, the upper edges 16A, 17A of the cover 3 are respectively bonded to the front and rear trunk regions of the absorbent structure 2 along hatched zone 51 somewhat off the waist-opening's peripheral edge to the crotch region. The cover 3 is dimensioned to have its height H smaller than the height h of the diaper 1 illustrated by FIG. 1 so that the upper edges 16A, 17A may be bonded to the absorbent structure 2 along the hatched zone 51. Alternatively, the cover 3 having the same dimensions as in the case of FIG. 2 is shifted downwards relatively to the absorbent structure 2 so that the upper edges 16A, 17A can be bonded to the absorbent structure 2 along the hatched zone 51. In this case, the cover 3 serves to cover a lower portion of the absorbent structure 2 bounded by said hatched zone 51 so as to leave the remaining upper portion bounded by the hatched zone 51 exposed.

Figure 4:
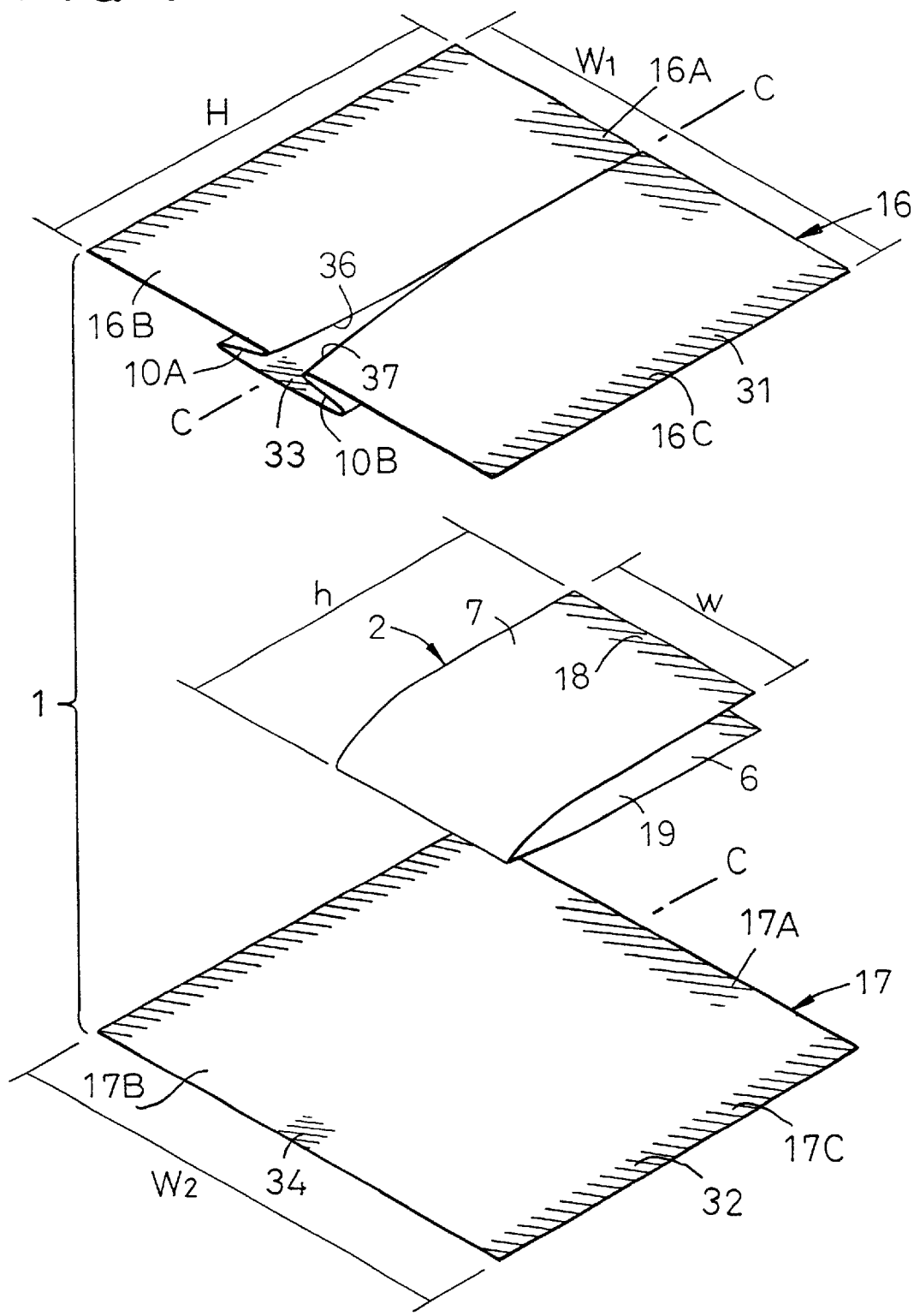
FIG. 4 is a view similar to FIG. 2 illustrating still another embodiment of the disposable diaper according to the invention.

FIG. 4 is a view similar to FIG. 2 illustrating still another embodiment of the invention. According to this embodiment, it is only the front sheet 16 that is formed with the Z- and inverted Z-cross-section pleats 10A, 10B, and the rear sheet 17 is identical, in shape and size, to the front sheet in its pleated state. The pleats 10A, 10B of the front sheet 16 have their crests 36, 37 lying more closely adjacent to each other transversely of the diaper 1 than in the case of FIG. 2. Substantially, these crests 36, 37 are in contact with each other. It should be noted here that said crests 36, 37 are shown in FIG. 4 as they are separated from each other in order to facilitate specific configurations of the respective pleats 10A, 10B to be understood. The absorbent structure 2 comprises the liquid-pervious topsheet 6, the liquid-impervious backsheet 7 and the liquid-absorbent core 8 (not shown) disposed between these two sheets 6, 7 wherein all these components are rectangular. The absorbent structure 2 is folded in two with the topsheet 6 inside so as to have a width w and a height h. Both the width w and the height h are smaller than the widths $W_1$, $W_2$ and the height H of the front and rear sheets 16, 17. The absorbent structure 2 is provided along its upper edge 18 extending transversely thereof and the side edges 19 extending vertically thereof with elastic members (not shown) in operative association with the waist-opening and the leg-openings, respectively. These elastic members are bonded to the upper edge 18 and the side edges 19 with appropriate tensions. The front and rear sheets 16, 17 placed upon each other with the absorbent structure 2 interposed therebetween have their upper edges 16A. 17A bonded to the front and rear sides, respectively, of the absorbent structure 2 along its upper edge 18. The front and rear sheets 16, 17 are directly bonded to each other along their side edges 16C, 17C and along middle portions 33, 34 of their lower edges 16B, 17B. Referring to FIG. 4, these zones along which the front and rear sheets 16, 17 are directly bonded to each other are indicated by hatches. The diaper 1 according to this embodiment is more advantageous than those of FIGS. 1 and 2 in that a structure of the absorbent structure 2 is simplified, an amount of sheet material required to make the rear sheet 17 can be reduced and this contributes to reduction of the manufacturing cost.

To exploit the invention, the liquid-pervious topsheet 6 of the absorbent structure 2 may be made of a nonwoven fabric or a apertured plastic sheet and the liquid-impervious backsheet may be made of a plastic sheet. The liquid-absorbent core 8 may be formed by fluff pulp fibers or a mixture of fluff pulp fibers and water-absorptive polymer particles. The front and rear sheets 16, 17 of the cover 3 may be made of a sheet material such as a woven fabric, a nonwoven fabric, a plastic sheet or a laminate of these sheets. These sheets 16, 17 are preferably of air-pervious nature and, if necessary, the sheet material may be formed with a plurality of apertures each having an appropriate diameter unless these apertures remarkably affect the desired function of the cover 3 to conceal the absorbent structure 2. The upper edges 16A, 17A of the cover 3 may be provided with elastic members, respectively, extending circumferentially of the respective trunk regions and bonded thereto with appropriate tension. These elastic members may be provided in addition to the elastic members 13 provided on the absorbent structure 2 or may replace these elastic members 13.

The disposable pull-on diaper according to the invention has a trunks-shaped cover which comprises a pair of rectangular sheets placed upon each other and these sheets are formed with respective pairs of pleats having Z-shaped and inverted Z-shaped cross-sections extending in parallel one to another. Such cover does not restrict free movement of the wearer's legs since the pleats are free to flare as wearer's legs move. With respect to its structure, the cover according to the invention is effectively simplified to reduce the cost conventionally required to make the cover of prior art.

What is claimed is:

1. A pull-on disposable diaper comprising:
   an absorbent structure having:
      a liquid-pervious topsheet;
      a liquid-impervious backsheet; and
      a liquid-absorbent core disposed between the liquid-pervious topsheet and the liquid-impervious backsheet so as to define a front body region for contacting a wearer's belly, a rear body region for contacting a wearer's back, and a crotch region extending between said front and rear body regions; and
   a trunks-shaped cover at least partially covering said absorbent structure,
   said absorbent structure being folded upon itself along said crotch region with said topsheet inside so as to have opposite side edges extending in a vertical direction of the diaper and longitudinal ends of said front and rear body regions extending between said opposite edges,
   said trunks-shaped cover comprising:
      a first sheet for covering at least a portion of said front body region and a front side of said crotch region; and
      a second sheet for covering at least a portion of said rear body region and a rear side of said crotch, said first and second sheets respectively having opposite side edges extending in said vertical direction of the diaper and upper and lower edges extending transversely of the diaper, said first and second sheets being bonded to each other along their opposite side edges and transversely middle zones of their lower edges to define a trunks-shape, and said first and second sheets having respective inner surfaces of their upper edges bonded to front and rear sides of said absorbent structure respectively,
   at least one of said first and second sheets having a pair of pleats extending the entire vertical length of the trunks and symmetrically with respect to a center line dividing a width of the diaper in two, said pair of pleats having a Z-shaped cross-section and inverted Z-shaped cross-section, respectively.

2. The diaper according to claim 1, wherein said front and rear regions are placed flat together and bonded to each other along their side edges so as to define a brief-shaped form having a waist-opening and a pair of leg-openings.

3. The diaper according to claim 1, wherein the transversely opposite side edges of said absorbent structure are superposed together and interposed between respective transversely opposite side edges of said trunks-shaped cover and the first and second sheets are bonded together along their respective side edges.

4. The diaper according to claim 1, wherein the longitudinally upper end of said absorbent structure is provided with elastic members which extend transversely of the diaper and are bonded thereto under tension.

* * * * *